United States Patent [19]

Lopez Ortiz et al.

[11] Patent Number: 6,100,393

[45] Date of Patent: Aug. 8, 2000

[54] PROCESS FOR PURIFYING 7-SUBSTITUTED AMINODEACETOXY-CEPHALOSPORINS THROUGH THE USE OF FILTRATION MEMBRANES

[75] Inventors: Juan Francisco Lopez Ortiz; Oscar Ferrero Barruego; Emiliano Gonzalez de Prado; Alejandro Vitaller Alba, all of Leon; Francisco Salto Maldonado, Madrid, all of Spain

[73] Assignee: Antibioticos, S.A., Madrid, Spain

[21] Appl. No.: 08/945,890

[22] PCT Filed: Mar. 14, 1997

[86] PCT No.: PCT/ES97/00065

§ 371 Date: Feb. 25, 1998

§ 102(e) Date: Feb. 25, 1998

[87] PCT Pub. No.: WO97/34902

PCT Pub. Date: Sep. 25, 1997

[30] Foreign Application Priority Data

Mar. 15, 1996 [ES] Spain .................................. 9600636

[51] Int. Cl.$^7$ .................. C07B 63/00; C07D 501/12; C07D 501/10; C07D 501/22

[52] U.S. Cl. .................. 540/220; 540/218; 540/222; 540/224; 540/225; 540/226; 540/227; 540/228; 540/229; 540/230; 540/215

[58] Field of Search ..................... 540/222, 224, 540/225, 226, 227, 228, 229, 230, 215, 220, 218

[56] References Cited

U.S. PATENT DOCUMENTS

| | | | |
|---|---|---|---|
| 4,058,660 | 11/1977 | Palmono Coll | 540/218 |
| 4,767,851 | 8/1988 | Palmono Coll | 540/218 |
| 5,070,194 | 12/1991 | Sasaoka | 540/214 |
| 5,512,454 | 4/1996 | Usher | 435/47 |
| 5,521,068 | 5/1996 | Lopez | 435/43 |

FOREIGN PATENT DOCUMENTS

| | | |
|---|---|---|
| 0055137 | 6/1982 | European Pat. Off. . |
| 1480850 | 7/1977 | United Kingdom . |
| 1232656 | 5/1991 | United Kingdom . |
| 9708175 | 3/1997 | WIPO . |

OTHER PUBLICATIONS

Zimmermann, Pharm. Ind. 47, 647–651, 1985.
Walsh, J. Allergy 47, 159, Mar. 1971.
Weiss, in "Detection of Bacterial Endotoxins With the Limulus Amebocyte Lysate Test" (Alan R. Liss, Inc), pp. 235–249, 1987.
Pfeiffer, Pharm. Ind 49, 1075, Oct. 1987.
Belter, Ed, "Bioseparations" (John Wiley & Sons, NY), 237–255, 1988.
Chemical Abstracts Printout for RN 859–07–4, 1999.
Chemical Abstracts Printout for RN 27255–72–7, 1999.
Kalyanpur, M., et al. "Isolation of Cephalosporin C from Fermentation Broths Using Membrane Systems and High–Performance Liquid Chromatography." Dev. Ind. Microbio., vol. 26, (1985) pp. 455–470.
Lau, A. H., et al. "Removal of Cephalosporins by Continuous Arteriovenous Ultrafiltration (CAVU) and Hemofiltration (CAVH)." The International Journal of Artificial Organs, vol. 12, No. 6 (1989) pp. 379–383.

*Primary Examiner*—Mark L. Berch
*Attorney, Agent, or Firm*—Ladas & Parry

[57] ABSTRACT

Process for purifying 7-substituted aminodeacetoxycephalosporins through the use of filter membranes. A process for purification by ultrafiltration and/or nanofiltration with a cut-off for molecular weights over 10,000 Dalton and preferably over 2000 Dalton is described. For example cephalosporin-G of increased purity, represented by a 6–8% increase in the HPLC titre, with a reduction of 50% in absorbance, is obtained using this technique. The invention makes it possible for the purified products to be used directly in the synthesis of other antibiotic compounds without the need for intermediate isolation.

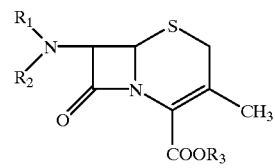

$R_1 = H$
$R_2 = C_6H_5 \cdot CH_2CO$
$\phantom{R_2 =} C_6H_5 \cdot O \cdot CH_2CO$
$R_3 = H, Na, K, ...$

16 Claims, No Drawings

PROCESS FOR PURIFYING 7-SUBSTITUTED AMINODEACETOXY-CEPHALOSPORINS THROUGH THE USE OF FILTRATION MEMBRANES

SCOPE OF THE INVENTION

In this invention the objective sought is the purification of 7-substituted aminodeacetoxycephalosporins through the use of a specific membrane filtering technology avoiding the quality of the final product being insufficient for subsequent use on account of being accompanied by a large number of impurities.

STATE OF THE ART

One of the most important stages of synthesis in the pharmaceutical manufacture of β-lactam antibiotics is the reaction of enlargement of the ring which provides access to the cephalosporin skeleton, which has a 6-membered heterocyclic structure, from penicillins in which the heterocyclic ring contains 5 atoms.

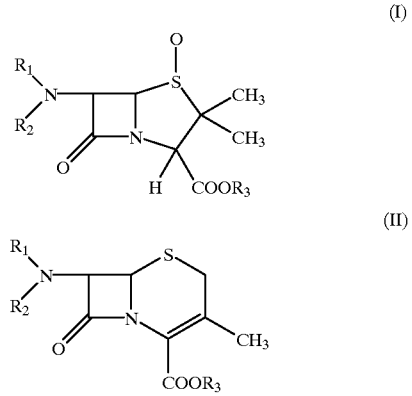

$R_1$ represents H; $R_2$ may be phenylacetyl, phenoxyacetyl, hexenoyl, 2-hexenoyl, 3-hexenoyl or octanoyl; $R_3$ may be H, a monovalent cation, or an alkyl having 1–3 C atoms.

Enlargement is a special case of the Pummerer reaction starting from penicillin sulphoxides (I), which through heating and the elimination of water give rise to the corresponding cephalosporins (II).

There are many publications which study this reaction in detail, based fundamentally on the already classical work by Morin et al. (J. Amer. Chem. Soc. 85, 1986 (1963); ibid. 91, 1401 (1969)), and other subsequent work in which this idea has been developed and commercialized (Chou. Tetrahedron Lett., 725 (1974); Koming et al. J. Org. Chem., 40, 1346 (1975); Claes et al. J. Antibiotics 32820 (1979); Noyori et al. 37, 3899 (1981)).

In all these there is reference to a greater or lesser extent to the coexistence alongside the desired reaction of other side reactions which unfortunately lead to the formation of a wide range of undesired products which appreciably contaminate the final compound.

The fact of bringing about heating which causes opening and subsequent closing in a molecule of extraordinary lability gives rise to great problems with purity of the final product, due to the existence of a large number of by-products, as shown in the extensive bibliography in the field (U.S. Pat. Nos. 3,275,626; 3,947,465; 4,000,129; 4,003,894; 4,159,267), among which mention should be made of:

products of isomerization of the double bond in the cefem ring decarboxylation products resin-forming products Because of this, most of the work published on enlargement of the ring centres on efforts to find reagents and reaction conditions which reduce the always high levels of by-products, and therefore increase the yield (EP 0169144 A2).

Ultrafiltration is a technique for separating dissolved molecules according to size by passing a solution through a sufficiently fine filter to retain most of the large molecules, allowing the small molecules and solvents to pass through. In this way ultrafiltration produces a retained fraction which is rich in large molecules and a filtrate which is largely free from such molecules.

One of the especially significant factors when performing selective purification using the ultrafiltration technique is selection of the membrane.

This choice is influenced by the chemical composition of the membrane itself, which makes it possible to work within specific ranges of pH, pressure and temperature, and also the specific molecular weight cut-off value, which brings about the selective separation of the molecules corresponding to the various products present.

As far as chemical composition is concerned, membranes of cellulose acetate, polysulphones, fluoropolymers and polyether sulphones which can be used over wide ranges of pressure, temperature and pH are known. As for the so-called cut-off value (the nominal molecular weight which will not pass) for each of these, the possibilities available cover an enormous range which includes approximate values of this parameter from 2000 to 500,000.

On the other hand the limits within which the technique of ultrafiltration lies are not clearly defined, so that at the lower limit, which depends fundamentally on the size of pore which ensures a specific cut-off value, mention is now made of a new technique called nanofiltration, which basically corresponds to a type of technique which uses membranes having nominal molecular weight cut-off values around 2000.

The fundamental difference between the process described in this invention in comparison with known ultrafiltration techniques applied to the purification of complex fermentation broths lies in the fact that in this invention the techniques of ultrafiltration and/or nanofiltration are applied to an aqueous solution originating from a stage of chemical synthesis in which the synthesized product has a greater specific purity than in the former case, and that despite this it has been possible to apply the technology of purification through membranes with a greater degree of specificity and therefore purification.

The process described offers a whole range of advantages, in addition to the high level of purity achieved when this separation is used in comparison with the conventional methods known hitherto, in which the use of chemical procedures brought about the use of solvents and/or reagents with consequent problems of toxicity and increased expense. The use of ultrafiltration makes it possible to work without organic solvents at all times and with low energy costs.

DESCRIPTION OF THE INVENTION

In this invention a technique of filtration on a specific membrane has been devised for the purification of aqueous solutions containing products obtained by a reaction of expanding the ring starting from penicillin sulphoxides.

In this invention we have used various ultrafiltration and nanofiltration membranes, in all cases having a cut-off value of less than 10,000, achieving highly satisfactory results with all the membranes tested. The level of purity achieved using these two techniques has been checked using determinations of titre (performed by HPLC chromatography) and colour (absorbance) on the product isolated by crystallization in every case from the aqueous starting solution and the solution obtained following treatment with the corresponding membrane.

Thus the use of ultrafiltration and nanofiltration membranes offers a very important purification procedure as demonstrated by the fact that the HPLC titre values for the product have been increased by 6–8% and the absorbance value (determined in all cases on a 2% solution in 0.1 M phosphate buffer having a pH of 8.0 at 415 nm) has been reduced by up to 50% with respect to the starting product. In this way, and by way of example, when starting with products having HPLC titre values close to 900 $\mu$g/mg and absorbance values of the order of 0.600, others having values in excess of 960 $\mu$g/mg for HPLC titre and an absorbance of less than 0.300 respectively are obtained when subjected to the purification process mentioned above.

The operating procedure followed in the experiments performed, which constitute the subject matter of this invention, correspond to a single methodology in that, starting from an aqueous solution containing the product known as 7-phenyl acetamide deacetoxycephalosporanic acid, together with the by-products resulting from the ring extension reaction, in order to obtain this product it is passed through the corresponding selected membrane under specific conditions of pH (in the range between 5 and 8), temperature (in the range 25–45° C.) and pressure (between 5 and 20 bar); after the volume has been reduced by between 2 and 10 times this yields an already purified solution from which a product corresponding to some HPLC titre and colour values, such as those mentioned above, is isolated.

In addition this invention describes a continuous process in which solutions purified in this way can be used for subsequent stages as intermediate compounds without the need for isolation. Processes in which these intermediate compounds obtained in accordance with the procedure described can be used are the preparation of 7-amino-deacetoxycephalosporanic acid, by both chemical and enzyme means, and in which this in turn can be used is the synthesis of cephalexin.

This invention is illustrated by the following examples which include some of the operating conditions tested.

EXAMPLE 1

The compound mentioned with an HPLC titre of 905 $\mu$g/mg and an absorbance of 0.550 was isolated by crystallization with 6 N sulphuric acid to a pH of 2.0 from an aqueous solution containing 97.5 g/l of 7-phenyl acetamide deacetoxycephalosporanic acid obtained by synthesis. An aliquot of the above solution, adjusted to pH 6.0 and 35° C., was passed through a GR-90 pp polysulphone-type membrane (DOW CHEMICAL) at a working pressure of 10 bar. Once the volume had been reduced 5-fold by successive concentration a permeate was obtained from which 7-phenyl acetamide deacetoxycephalosporanic acid having a HPLC titre value of 970 $\mu$g/mg and an absorbance of 0.280 was obtained by crystallization by adjusting the pH to 2.0 using 6 N sulphuric acid.

EXAMPLE 2

An aqueous solution containing 103.5 g/l of 7-phenyl acetamide deacetoxycephalosporanic acid obtained by synthesis was concentrated reducing the initial volume seven times using a membrane of the GR-90 pp type at a working pressure of 15 bar, a pH of 6.5 and a temperature of 30° C., and from this a product having an absorbance of 0.570 and an HPLC titre of 912 $\mu$g/mg was isolated by crystallization (as described in Example 1), yielding a permeate from which 7-phenyl acetamide deacetoxycephalosporanic acid with an HPLC titre of 980 $\mu$g/mg and a colour of 0.290 was crystallized at a pH of 2.0 using 6 N sulphuric acid.

EXAMPLE 3

The product named 7-phenyl acetamide deacetoxycephalosporanic acid which was crystallized out in a manner similar to that in Example 1, from an aqueous solution obtained by synthesis containing 88.3 g/l of the said product had an HPLC titre of 905 $\mu$g/mg and an absorbance of 0.540. When an aliquot of this solution at a pH of 6.0 and a temperature of 35° C. was passed through an ultrafiltration membrane of the polyether sulphone type, specifically that known as AES-5 (AMT) at a working pressure of 10 bar, a permeate was obtained, after a 6-fold reduction in the starting volume, from which 7-phenyl acetamide deacetoxycephalosporanic acid having an absorbance of 0.275 and an HPLC titre of 973 $\mu$g/mg was obtained by crystallization at a pH of 2.0 using 6 N sulphuric acid.

EXAMPLE 4

7-phenyl acetamide deacetoxycephalosporanic acid with an absorbance of 0.580 and an HPLC titre of 907 $\mu$g/mg was crystallized out in a manner similar to that in Example 1 from an aqueous solution obtained by synthesis containing 98 g/l of that product. When an aliquot of this solution was passed through a nanofiltration membrane of the sulphonated polysulphone type, specifically the one known as ASP-10 (AMT) a final permeate was obtained through successive concentration to reduce the starting volume 10-fold and operating under the conditions of pH 6.5, temperature 30° C. and pressure 15 bar, from which 7-phenyl acetamide deacetoxycephalosporanic acid with an HPLC titre of 980 $\mu$g/mg and an absorbance of 0.300 was isolated by crystallization at pH 2.0 using 6 N sulphuric acid.

EXAMPLE 5

Crystallization of an aqueous solution obtained by synthesis which contained 110 g/l of 7-phenyl acetamide deacetoxycephalosporanic acid at a pH of 2.0 using 6 N sulphuric acid resulted in a product which had an HPLC titre of 908 $\mu$g/mg and an absorbance of 0.550. An aliquot of this solution was adjusted to a pH of 7.5 and passed through a nanofiltration membrane, specifically G-50 (DESAL), maintaining the temperature at 25° C. and the working pressure at 12 bar, bringing about an 8-fold reduction in the starting volume. 7-phenyl acetamide deacetoxycephalosporanic acid having an HPLC titre of 978 $\mu$g/mg and an absorbance of 0.270 was isolated from the final permeate obtained by crystallization with 6 N sulphuric acid at pH 2.0.

EXAMPLE 6

93.5 g/l of the product called 7-phenyl acetamide deacetoxycephalosporanic acid with an HPLC titre of 865 $\mu$g/mg and an absorbance of 0.863 was obtained by crystallization from an aqueous solution obtained by synthesis, in a manner similar to that in Example 1. When an aliquot of this solution at a pH of 7.0 and a temperature of 25° C. was passed through a membrane of the GR-90 pp polysulphone type (DOW CHEMICAL) at a working pressure of 15 bar, a permeate was obtained after an 8-fold reduction in the starting volume, from which the corresponding 7-phenyl acetamide deacetoxycephalosporanic acid having HPLC titre and absorbance values of 930 μg/mg and 0.390 respectively was isolated by crystallization at pH 2.0 using 6 N sulphuric acid.

EXAMPLE 7

The product 7-7-phenyl acetamide deacetoxycephalosporanic acid having a titre of 935 μg/mg and an absorbance of 0.420 was crystallized out from an aqueous solution obtained by synthesis. An aliquot of the said solution was passed through a membrane of the polysulphone type, specifically that known as GR-90 pp (DOW CHEMICAL) to reduce the starting volume 7-fold, under the following operating conditions: pH=7.0, temperature=25° C., pressure=15 bar. In this way a permeate was obtained from which purified cephalosporin-G having HPLC titre and absorbance values of 985 μg/mg and 0.160 respectively was isolated by crystallization at a pH of 2.0 using 6 N sulphuric acid.

EXAMPLE 8

A permeate obtained as described in Example 1 was appropriately diluted with phosphate buffer solution to obtain a 7-phenyl acetamide deacetoxycephalosporanic acid concentration of the order of 40 g/l.

On the other hand a suspension of Penicillin G (Boehringer) in phosphate buffer solution was prepared in a proportion of 60 g of enzyme per liter of the buffer solution.

Enzyme hydrolysis was carried out by placing the cephalosporin-G solution in contact with a fifth part by volume of Boehringer amidase suspension.

Once conversion was complete the enzyme was recovered by filtration and half the volume of methanol was added to the filtrate, followed by crystallizing out 7-aminodeacetoxycephalosporanic acid in a yield of 95% by adjusting to pH 4 using 12 N hydrochloric acid.

What is claimed is:

1. In a process for the purification of a mixture of reaction products comprising a 7-substituted aminodesacetoxycephalosporin, wherein the mixture is formed from a penicillin sulphoxide in a ring expansion reaction that produces the reaction mixture as an aqueous solution comprising said desacetoxycephalosporin and contaminating by-products of said ring expansion reaction, said penicillin sulphoxide comprising the following formula I:

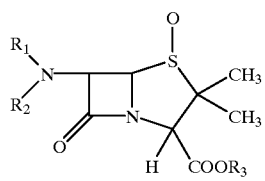

(I)

wherein $R_1$ is H; $R_2$ is phenylacetyl, phenoxyacetyl, hexenoyl, 2-hexenoyl, 3-hexenoyl or octanoyl; $R_3$ is H, a monovalent cation, or an alkyl having 1–3 C atoms, the improvement comprising the step of filtering said aqueous solution through a membrane that filters contaminating by-products having a molecular weight above 10,000 Daltons from the aqueous solution to form a filtered solution comprising a purified desacetoxycephalosporin.

2. A process for the purification of a mixture of reaction products comprising a 7-substituted aminodesacetoxycephalosporin, wherein the mixture is formed from a penicillin sulphoxide in a ring expansion reaction that produces the reaction mixture as an aqueous solution comprising said desacetoxycephalosporin and contaminating by-products of said ring expansion reaction, said penicillin sulphoxide comprising the following formula I:

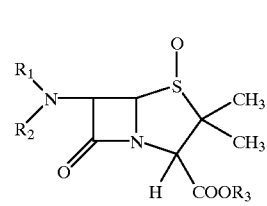

(I)

wherein $R_1$ is H; $R_2$ is phenylacetyl, phenoxyacetyl, hexenoyl, 2-hexenoyl, 3-hexenoyl or octanoyl; $R_3$ is H, a monovalent cation, or an alkyl having 1–3 C atoms, the process consisting essentially of filtering said aqueous solution through a membrane that filters the contaminating by-products having a molecular weight above 10,000 Daltons from the aqueous solution to form a filtered solution comprising a purified desacetoxycephalosporin.

3. A process comprising
  (a) providing a mixture of reaction products comprising a 7-substituted aminodesacetoxycephalosporin, said mixture being formed from a penicillin sulphoxide in a ring expansion reaction that produces the mixture as an aqueous solution comprising said desacetoxycephalosporin and by-products of said ring expansion reaction, said penicillin sulphoxide comprising the following formula I:

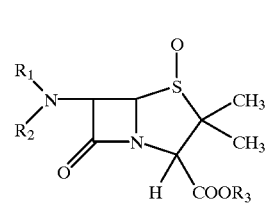

(I)

wherein $R_1$ is H; $R_2$ is phenylacetyl, phenoxyacetyl, hexenoyl, 2-hexenoyl, 3-hexenoyl or octanoyl; $R_3$ is H, a monovalent cation, or an alkyl having 1–3 C atoms;
  (b) filtering the aqueous solution by passing it through a membrane that filters the by-products having a molecular weight above 10,000 Daltons from the aqueous solution to form a filtered solution comprising a purified descatoxycephalosporin; and
  (c) synthesizing 7-amino-desacetoxycephalosporanic acid from the filtered solution without isolation of the purified desacetoxycephalosporin.

4. A process as claimed in claim 3, wherein the desacetoxycephalosporin is 7-phenyl acetamide desacetoxycephalosporanic acid.

5. A process as claimed in claim 3 further comprising (d) synthesizing cephalexin from the 7-amino-desacetoxycephalosporanic acid synthesized in step (c).

6. A process as claimed in claim 5, wherein the desacetoxycephalosporin is 7-phenyl acetamide desacetoxycephalosporanic acid.

7. A process as claimed in claim 2, wherein the solution formed by the filtering step can be concentrated to form a permeate in which the desacetoxycephalosporin is present with a purity in excess of 96%.

8. A process as claimed in claim 7, wherein the desacetoxycephalosporin is 7-phenyl acetamide desacetoxycephalosporanic acid.

9. A process as claimed in claim 1, wherein the filtering step is performed within a pH range of between 5 and 8.0 at a temperature of between 20 and 45° C. and at a pressure of between 5 and 15 bar.

10. A process as claimed in claim 1, wherein the filtered solution formed by the filtering step can be concentrated to form a permeate in which the desacetoxycephalosporin is present with a purity in excess of 96%.

11. A process as claimed in claim 10, wherein the desacetoxycephalosporin is 7-phenyl acetamide desacetoxycephalosporanic acid.

12. A process as claimed in claim 1, wherein the desacetoxycephalosporin is purified from the mixture of reaction products without use of an organic solvent.

13. A process as claimed in claim 1, wherein the filtering step is carried out under conditions and with the membrane selected such that the filtered solution, when treated with an acid to provide it with an acid pH, forms a crystallized product that has a titer value, as measured by high performance liquid chromatography, that is at least 6% higher than a titer value of a crystallized product formed from the aqueous solution when treated with the acid to provide it with the acid pH.

14. A process as claimed in claim 1, wherein the aqueous solution, prior to filtering through the membrane, has a concentration of said desacetoxycephalosporin below 200 g/l.

15. A process as claimed in claim 1, wherein the aqueous solution, prior to filtering through the membrane, has a concentration of said desacetoxycephalosporin between 70 and 120 g/l.

16. A process as claimed in claim 1, wherein the membrane filters by-products having a molecular weight above 2,000 Daltons.

* * * * *